US005540698A

United States Patent [19]
Preissman

[11] Patent Number: 5,540,698
[45] Date of Patent: Jul. 30, 1996

[54] SYSTEM AND METHOD FOR SECURING A MEDICAL CABLE

[75] Inventor: Howard E. Preissman, Dallas, Tex.

[73] Assignee: AMEI Technologies Inc., Wilmington, Del.

[21] Appl. No.: 123,752

[22] Filed: Sep. 16, 1993

Related U.S. Application Data

[63] Continuation-in-part of Ser. No. 52,058, Apr. 21, 1993, Pat. No. 5,449,361, and Ser. No. 52,059, Apr. 21, 1993, abandoned.

[51] Int. Cl.$^6$ .................................................. A61B 17/56
[52] U.S. Cl. ........................................................... 606/103
[58] Field of Search .............................. 606/86, 139, 103, 606/207, 74; 72/410

[56] References Cited

U.S. PATENT DOCUMENTS

| | | | |
|---|---|---|---|
| 409,327 | 8/1889 | Maeurer | 403/374 |
| 409,721 | 8/1889 | Williams, Jr. . | |
| 1,234,435 | 7/1917 | Wood | 403/374 |
| 1,258,580 | 3/1918 | Lassiter . | |
| 1,304,620 | 5/1919 | Steinkoenig . | |
| 1,346,940 | 7/1920 | Collins . | |
| 1,347,579 | 7/1920 | Henrikson . | |
| 1,388,716 | 8/1921 | Hughes . | |
| 1,641,077 | 8/1927 | Fouquet . | |
| 1,717,766 | 6/1929 | Eimler . | |
| 2,049,361 | 7/1936 | Ericsson . | |
| 2,279,068 | 4/1942 | Sieberandt . | |
| 2,291,413 | 7/1942 | Siebrandt . | |
| 2,455,609 | 12/1948 | Scheib . | |
| 2,509,290 | 5/1950 | Elvin et al. . | |
| 2,883,096 | 4/1959 | Dawson . | |
| 2,928,395 | 3/1960 | Forbes et al. . | |
| 3,035,476 | 5/1962 | Fogden . | |
| 3,035,583 | 5/1962 | Hirsch et al. . | |
| 3,078,755 | 2/1963 | Chace, Jr. . | |
| 3,111,945 | 11/1963 | Von Solbrig . | |

(List continued on next page.)

FOREIGN PATENT DOCUMENTS

| | | |
|---|---|---|
| 218602 | 9/1956 | Australia . |
| 1158422 | 12/1983 | Canada . |
| 0019062 | 3/1980 | European Pat. Off. ........ A61B 17/18 |
| 999646 | 2/1952 | France . |
| 1177769 | 9/1964 | Germany . |
| 1958429 | 7/1971 | Germany . |
| 3146634 | 6/1983 | Germany . |
| 506401 | 5/1976 | Russian Federation . |
| 123046 | 10/1926 | Switzerland . |
| 275268 | 8/1951 | Switzerland . |
| 163340 | 6/1921 | United Kingdom . |
| 579288 | 7/1946 | United Kingdom . |
| 727988 | 4/1955 | United Kingdom . |
| 958284 | 5/1964 | United Kingdom . |

OTHER PUBLICATIONS

Danek Medical, Inc. ©1994, "Danek® Titanium Cable System" (LIT–SONG–TSS–93) (two pages).
Danek Medical, Inc. ©1994, "Danek© Cable Instruments" (LIT–DC1–94) (two pages).

Primary Examiner—Tamara L. Graysay
Attorney, Agent, or Firm—Baker & Botts L.L.P.

[57] ABSTRACT

A system and method for securing a medical cable and a loop about a specified portion of a patient's body are disclosed. The system may include a medical cable, a crimp-locking crimp, a releasable cable securing device, and a cable tensioner. Additionally, a crimper-cutter may be used as part of the system. The releasable cable securing device may include a body having a cable-receiving channel, a wedging chamber and a wedging member that cooperate to allow a cable to be moved in a first direction, but not moved in a second direction. The cable may be released from the releasable cable securing device by depressing a portion of the wedging member. The crimper cutter may include a first head formed to have a crimping channel and a blade member, and a second head formed to force the neck of a crimp into the crimping channel and then on to the blade member.

12 Claims, 5 Drawing Sheets

5,540,698

Page 2

U.S. PATENT DOCUMENTS

| | | |
|---|---|---|
| 3,215,768 | 11/1965 | Murphy . |
| 3,233,800 | 2/1966 | Catania . |
| 3,323,208 | 6/1967 | Hurley, Jr. . |
| 3,507,270 | 4/1970 | Ferrier . |
| 3,587,585 | 6/1971 | Ceravolo . |
| 3,762,418 | 10/1973 | Wasson . |
| 3,802,438 | 4/1974 | Wolvek . |
| 3,892,241 | 7/1975 | Leveen . |
| 3,910,281 | 10/1975 | Kletschka et al. . |
| 3,952,377 | 4/1976 | Morell . |
| 3,965,541 | 6/1976 | Davison . |
| 3,976,079 | 8/1976 | Samuels et al. . |
| 3,993,109 | 11/1976 | Fortsch . |
| 4,050,464 | 9/1977 | Hall . |
| 4,084,625 | 4/1978 | Brinegar . |
| 4,128,100 | 12/1978 | Wendorff . |
| 4,200,126 | 4/1980 | Fish . |
| 4,246,771 | 1/1981 | Covill et al. ............................... 72/410 |
| 4,283,933 | 8/1981 | Wiener . |
| 4,291,698 | 9/1981 | Fuch et al. . |
| 4,333,649 | 6/1982 | Vaughn et al. . |
| 4,387,489 | 6/1983 | Dudek . |
| 4,412,474 | 11/1983 | Hara . |
| 4,509,233 | 4/1985 | Shaw . |
| 4,527,554 | 7/1985 | Klein . |
| 4,557,259 | 12/1985 | Wu . |
| 4,570,618 | 2/1986 | Wu . |
| 4,587,963 | 5/1986 | Leibinger et al. . |
| 4,592,355 | 6/1986 | Antebi . |
| 4,625,717 | 12/1986 | Covitz . |
| 4,643,178 | 2/1987 | Nastari et al. . |
| 4,712,770 | 12/1987 | Wiederkehr . |
| 4,716,630 | 1/1988 | Skyba ..................... 24/134 R |
| 4,716,886 | 1/1988 | Schulman et al. . |
| 4,741,330 | 5/1988 | Hayhurst . |
| 4,750,492 | 6/1988 | Jacobs . |
| 4,773,402 | 9/1988 | Asher et al. . |
| 4,790,303 | 12/1988 | Steffee . |
| 4,889,110 | 12/1989 | Galline et al. ............................ 606/69 |
| 4,889,320 | 12/1989 | Pasbrig ..................... 254/252 |
| 4,901,721 | 2/1990 | Hakki ............................... 606/103 |
| 4,946,462 | 8/1990 | Watanabe ............................... 606/148 |
| 4,966,600 | 10/1990 | Songer et al. ............................. 606/74 |
| 4,969,895 | 11/1990 | McLeod et al. ........................ 606/96 |
| 5,052,094 | 10/1991 | Plasse et al. . |
| 5,057,113 | 10/1991 | Mingozzi ............................... 606/103 |
| 5,059,207 | 10/1991 | Shah ....................... 606/223 |
| 5,089,012 | 2/1992 | Prou ....................... 606/224 |
| 5,092,868 | 3/1992 | Mehdian ............................... 606/74 |
| 5,116,340 | 5/1992 | Songer et al. ............................. 606/103 |
| 5,127,144 | 7/1992 | Plasse et al. . |
| 5,133,738 | 7/1992 | Korthoff et al. ........................ 606/224 |
| 5,199,146 | 4/1993 | Grover et al. . |
| 5,312,410 | 5/1994 | Miller et al. ............................... 606/86 |
| 5,395,374 | 3/1995 | Miller et al. ............................... 606/74 |

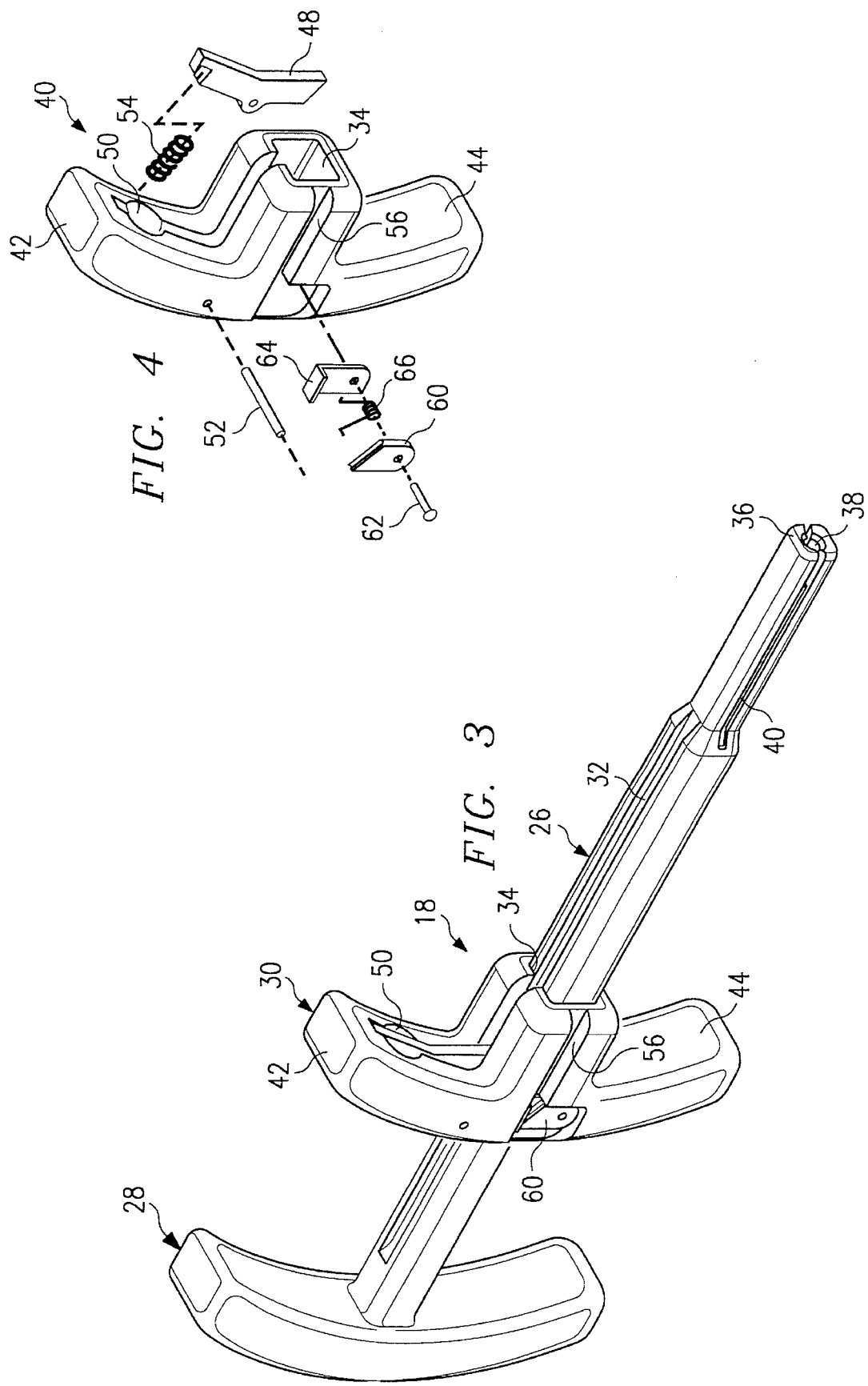

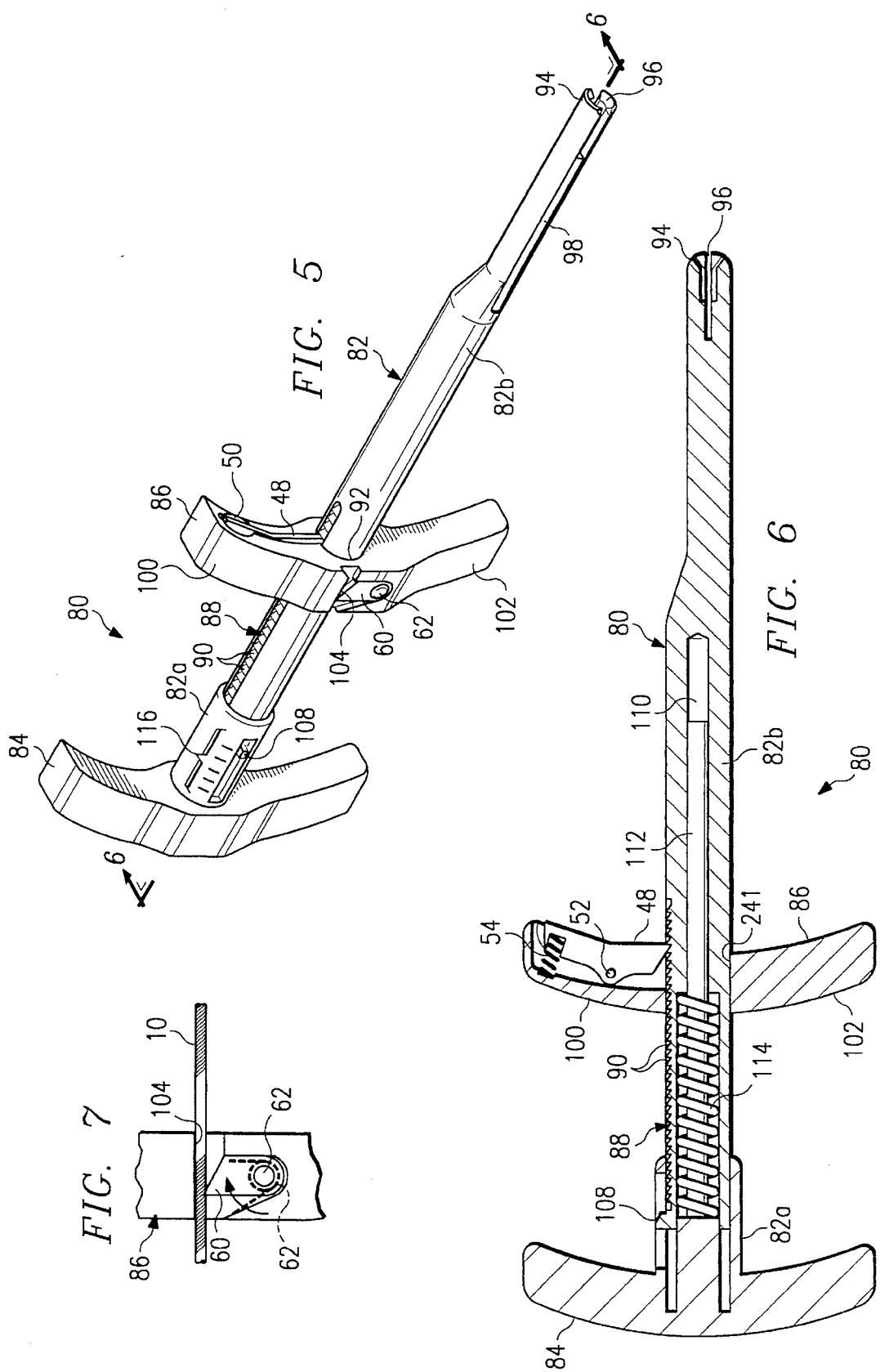

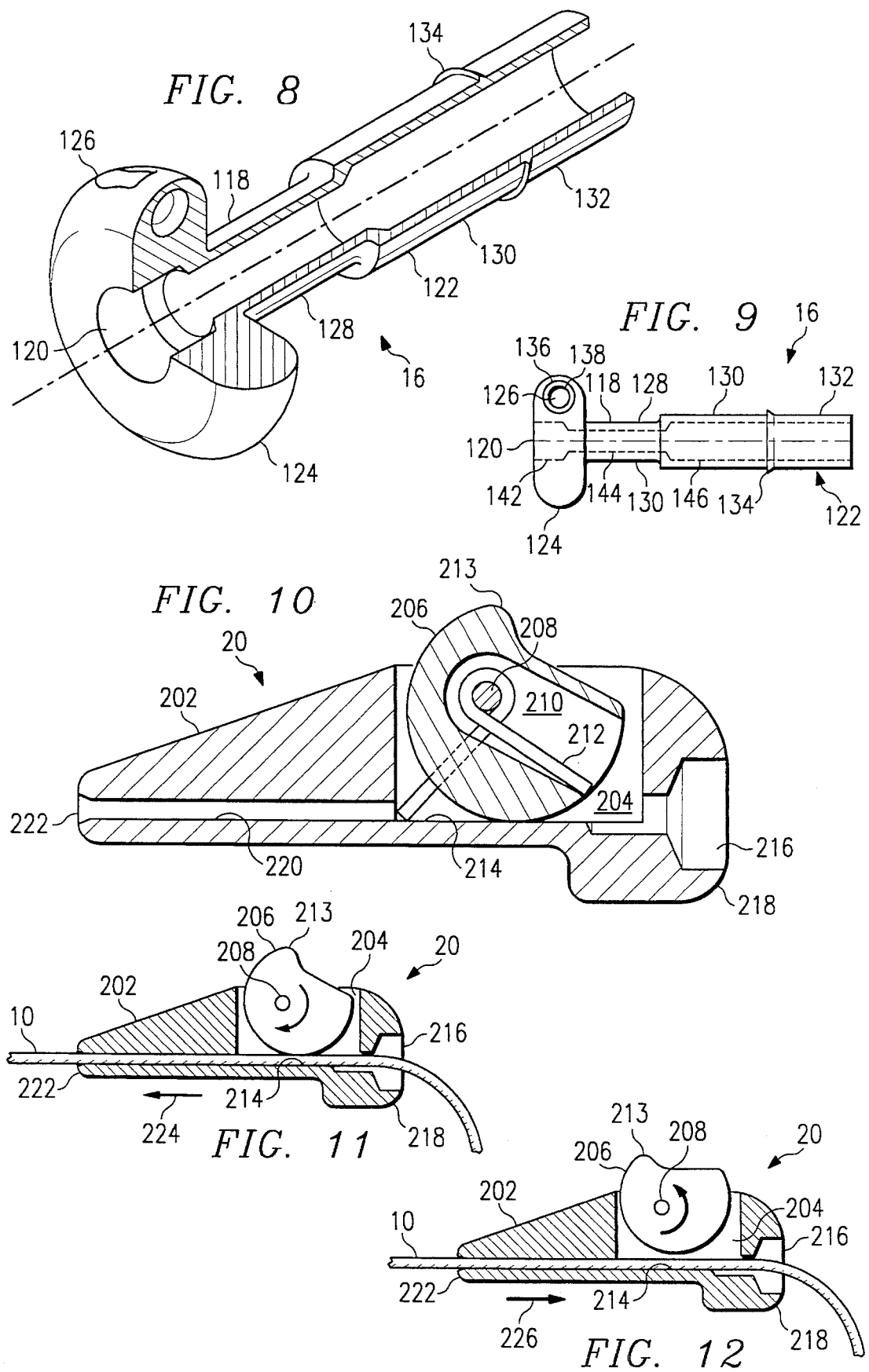

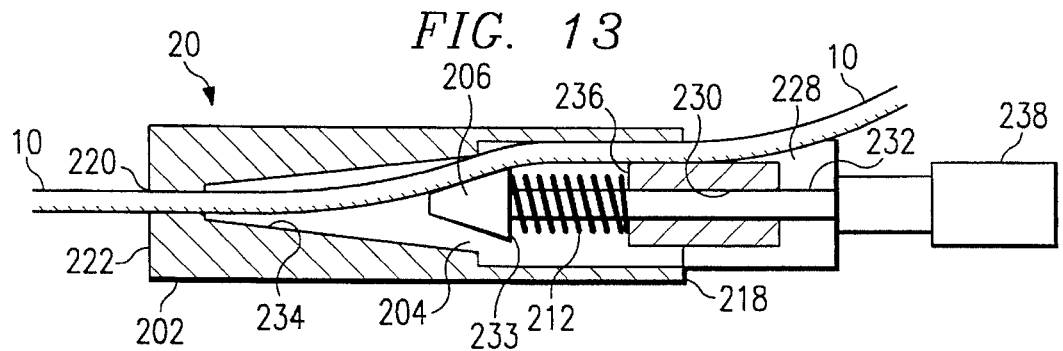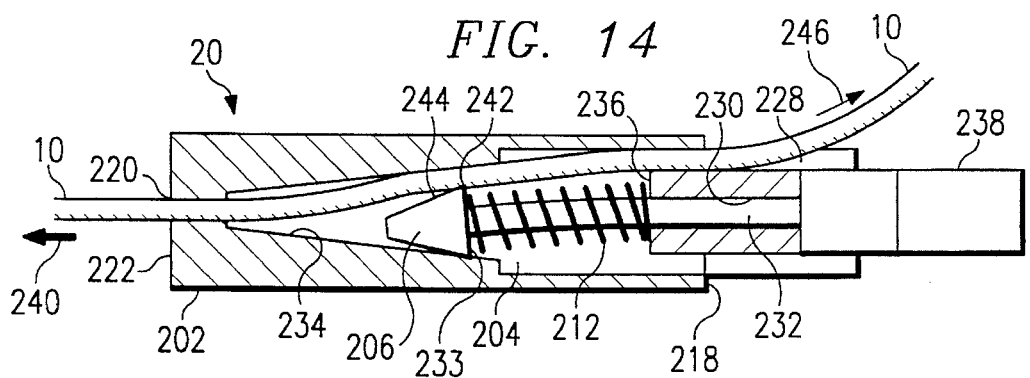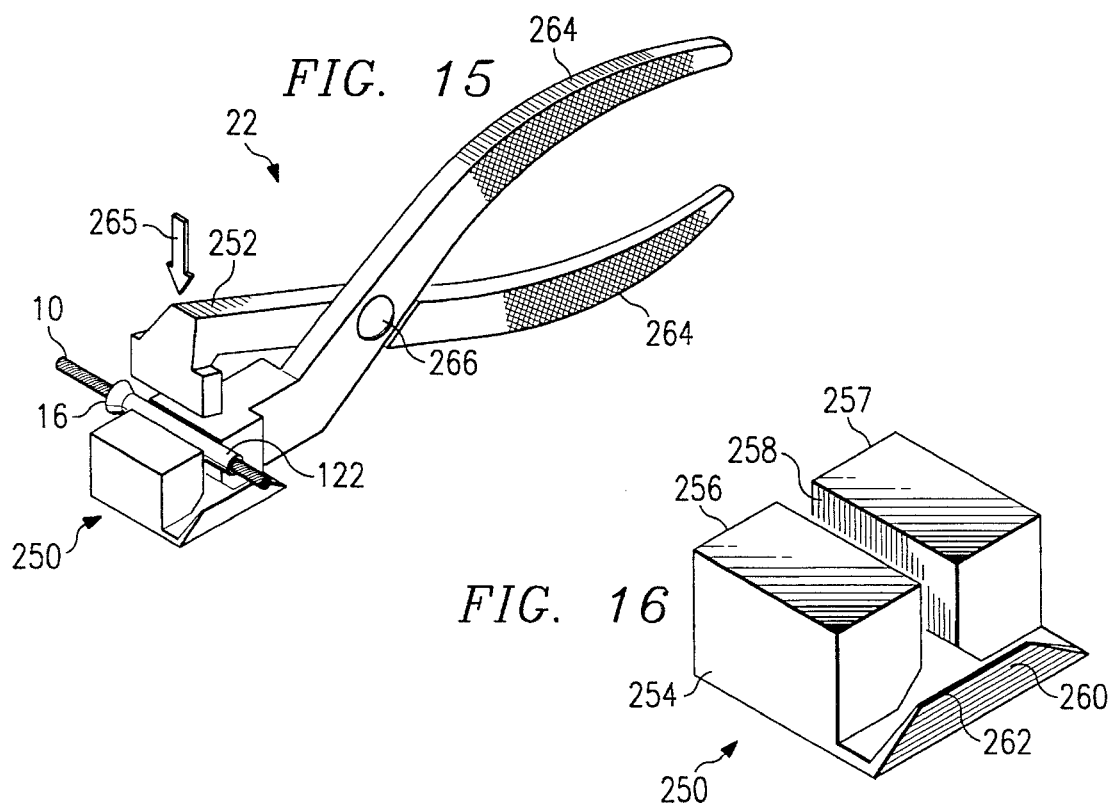

SYSTEM AND METHOD FOR SECURING A MEDICAL CABLE

RELATED APPLICATIONS

This application is a continuation-in-part patent application of co-pending patent applications Ser. No. 08/052,058 entitled *Orthopedic Cable Tensioner* now U.S. Pat. No. 5,449,361 and Ser. No. 08/052,059 entitled *Surgical Cable Crimp*, now abandoned, both filed Apr. 21, 1993, and is related to co-pending patent applications Ser. No. 08/052,191 entitled *Surgical Cable Leader and Terminations* (Attorney's Docket 90928-0205) now abandoned, and Ser. No. 08/051,179 entitled *Surgical Cable and Cable Clamp* (Attorney's Docket 90928-0181) now abandoned.

TECHNICAL FIELD OF THE INVENTION

This invention relates to surgically implanted wires and cables and more particularly relates to improved methods and apparatus for use in surgically installing wires and cables at selected locations in a patient's body.

BACKGROUND OF THE INVENTION

Surgical or medical wires and cables are used in a variety of surgical procedures, for example, reconstructive spine surgery such as fusions, spinal trauma surgery, total hip arthroplasty, fracture fixation, open heart surgery for closures of the sternum, oral and facial surgery to fix mandibular fractures and the like, and other surgical procedures. Often, medical cables and wires are used to encircle or loop about bones to hold them together for healing or fusion in some types of spinal surgery. For purposes of this application, "cable" includes monofilament and single strand wire along with multi-filament and multi-strand cable and wire ropes.

In some surgical procedures, it is desirable to provide a tensile force to selected portions of the patient's body such as to adjacent vertebrae. This may be accomplished by placing loops formed of medical cable about the vertebrae. In placing the loops around the vertebrae with the desired tension on the vertebrae, it is frequently necessary to pass the cables sublaminarly, to apply the desired tension on the vertebrae through the cables, and then secure the cables in loops. One method of accomplishing these tasks is for the surgeon to pass a suture sublaminarly, to secure the suture to a mid-section of the cable, pull the suture with the attached cable back under the lamina of the vertebrae, and then cut the suture and cable so that two cables exist under the lamina of the patient. The cables can then be looped about the vertebrae and tightened by hand with the surgeon plucking the cables to determine the tension. After pulling the cables until the surgeon determines that the desired tension is applied, the surgeon attempts to secure the cables in their respective loops while maintaining the tension thereon.

Problems sometimes occur with placing the correct tension on the medical cables during installation. Conventional systems for attaching medical cables to selected portions of the patient's body have experienced problems with the cables being applied too tightly and creating vascular necrosis of the bone around the cables. At the same time, medical cables must be tight enough to achieve the desired mechanical fixation. Many conventional systems are difficult to manipulate and surgeons have experienced problems in properly positioning the cables while at the same time applying the desired tension and then securing the cables in the loops with that desired tension still applied. Many currently available tensioner products do not provide direct feedback to a surgeon concerning the amount of tension being applied to the cable. Securing the cables in their respective loops with conventional products and methods has also involved problems.

One method for securing the cables in their respective loops has been to provide a permanent loop on one end of the cables. This method involves forming a small loop on one end of the cable and securing the small loop with a crimp, and then passing the end opposite the small loop through the small loop in an arrangement similar to a cowboy's lasso. Then a crimp member with a flange may be placed on the cable opposite the small loop and slid along the cable until snug against the small loop member. Then after applying the desired tension as accurately as possible with conventional systems, the surgeon attempted to crimp the crimp member while maintaining the desired tension so that a secured loop is formed with the desired tension. This method involves two crimp members and has two parts of the cables resting against each other which may lead to increased wear of the cable and increased likelihood of premature failure. Additionally, it may be difficult to accurately maintain the tension on the cable while the cables are crimped.

Another method for securing the cable is to provide bar member with two transverse apertures. A stop member is attached to one end of the cable and then the other cable end is passed through one of the apertures until a stop rests against the bar member. The cable end opposite the stop member forms a loop and is then passed through the other aperture and then through a crimp member. The crimp member is placed snugly against the bar member and crimped while the surgeon attempts to maintain the desired tension on the cable. Among the shortcomings of this method may be the difficulty in holding all the parts with surgical instruments during this procedure. Additionally, this method and the previously described method do not protect against fraying once the cable is cut. See U.S. Pat. No. 5,116,340, which is incorporated by reference for all purposes.

Therefore, a need has arisen for a surgical installation system and apparatus that efficiently secure a medical cable in a loop, uses a small number of parts, is easily handled by a minimum number of surgical instruments, does not allow the cable to rest against other portions of the cable, helps prevent fraying, and helps to assure that the desired tension is produced in the secured loop.

SUMMARY OF THE INVENTION

In accordance with the present invention, the disadvantages and problems associated with the previously available medical cable installation systems and apparatuses have been substantially reduced or eliminated by use of the present system and apparatuses. The present invention includes components and methodologies for applying support to selected portions of a patient's body.

In accordance with one aspect of the present invention, a system for allowing an operator to secure a medical cable in a loop about a specified portion of a patient's body with a given tension is provided. The system may include a tensioner, a crimp-locking crimp, and a releasable cable securing apparatus.

In accordance with another aspect of the present invention, a crimper-cutter is provided. The crimper-cutter may be used to crimp a crimp-locking crimp and cut a portion of the crimp-locking crimp with one motion of one surgical instrument.

In accordance with another aspect of the present invention, a method is provided for securing a medical cable in a loop about a selected region of the patient's body.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 is an isometric drawing showing a cable tensioner according to one aspect of the present invention;

FIG. 4 is an isometric drawing with portions exploded away showing the second slidable handle used with the tensioner of FIG. 1;

FIG. 5 is an isometric drawing of a cable tensioner incorporating an additional embodiment of a tensioner according to one aspect of the present invention;

FIG. 6 is a drawing in section and in elevation with portions broken away taken along line 6—6 of FIG. 5;

FIG. 7 is a schematic representation showing a medical cable engaged with a second slidable handle of the tensioner shown in FIGS. 5 and 6;

FIG. 8 is an isometric drawing in section of a crimp-locking crimp according to one aspect of the present invention;

FIG. 9 is a schematic view in elevation of one aspect of the present invention showing one embodiment of the crimp-locking crimp;

FIG. 10 is a schematic view in cross-section and elevation showing one embodiment of a releasable cable securing device according to one aspect of the present invention;

FIG. 11 is a schematic drawing of the releasable cable securing device of FIG. 10 with a net force applied in a first direction;

FIG. 12 is a schematic drawing of the releasable cable securing device of FIG. 10 with a net force applied in a second direction;

FIG. 13 is a schematic view in cross-section and elevation of a second embodiment of a releasable cable securing device according to one aspect of the present invention with the biasing release member in the release position;

FIG. 14 is a schematic view in cross-section and elevation of a second embodiment of a releasable cable securing device according to one aspect of the present invention with biasing release member in the engaging position;

FIG. 15 is a schematic view of one embodiment of a crimper-cutter according to one aspect of the present invention; and FIG. 16 is a schematic view of the crimping-cutting head of the crimper-cutter of FIG. 15.

DETAILED DESCRIPTION OF THE INVENTION

The preferred embodiment of the present invention and its advantages are best understood by referring to FIGS. 1–16 of the drawings, like numerals being used for like and corresponding parts of the various drawings.

Figure 1:
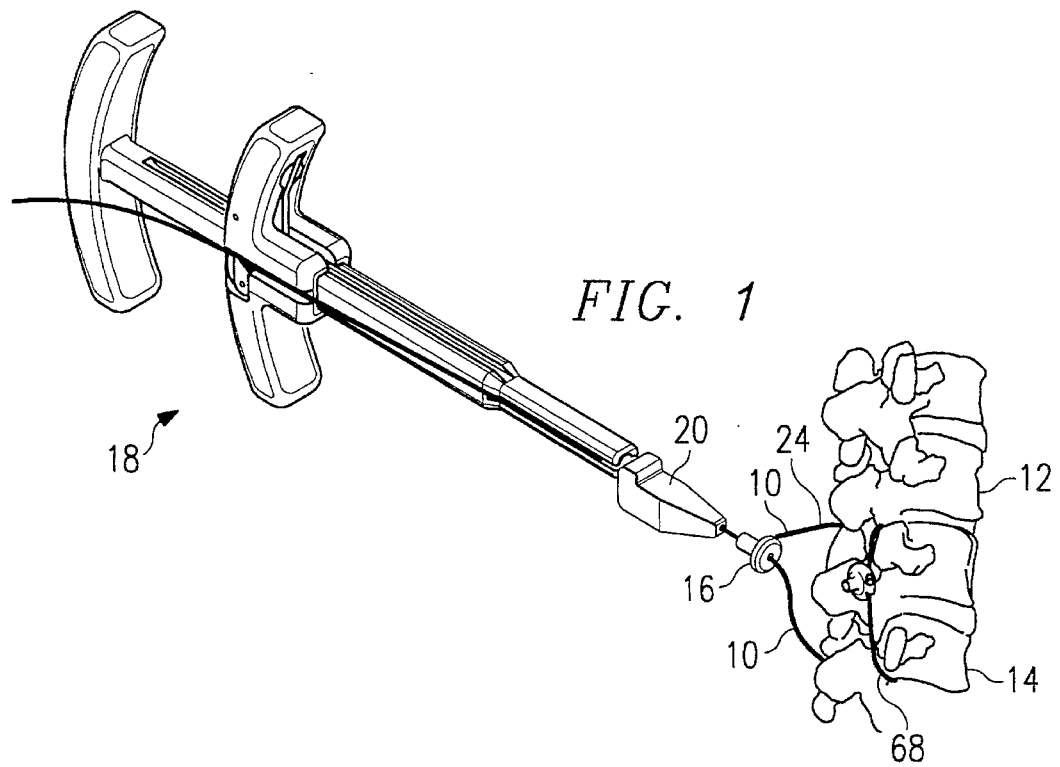
FIG. 1 is a schematic view of one aspect of the present invention showing a loop being formed around a specified portion of a patient's body using a medical cable, crimp-locking crimp, releasable cable securing device, and a tensioner.
Figure 2:
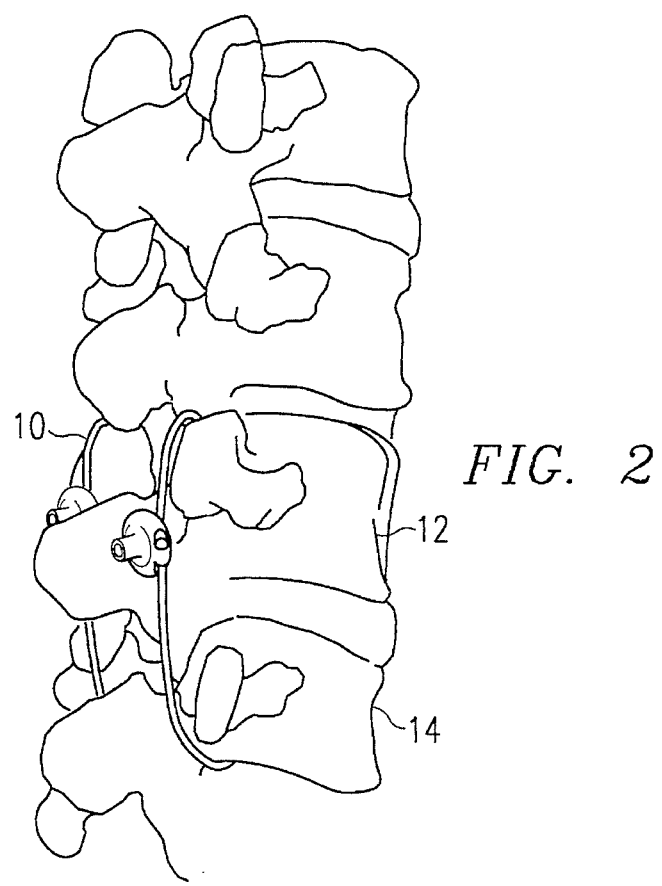
FIG. 2 is a schematic view of one aspect of the present invention showing a loop formed about a patient's vertebra.

In accordance with one aspect of the present invention, a system is provided for the installation of medical cables 10 about a portion of a patient's body such as vertebrae 12 and 14 (FIG. 2). The system involves a plurality of components including cable 10, crimp-locking crimp 16, cable tensioner 18, and releasable medical cable securing apparatus or crimp 20 (FIG. 1). Additionally, crimper-cutter 22 may be included in the system. Other devices such as a cable leader (not shown) may be used with this system. Another aspect of the present invention involves a method for securing cable 10 in a loop about a portion of a patient's body such as vertebrae 12 and 14.

CABLE TENSIONER

Cable tensioner 18 is preferably used with a medical cable 10 and a crimp-locking crimp 16 to trap the desired amount of tension in a loop formed by medical cable 10 and crimp 16. Medical cable 10, crimp-locking crimp 16, first loop 24, and tensioner 18 are shown in FIG. 1. The use of cable tensioner 18 to install medical cable 10 to selected portions of a patient's body and to trap the desired amount of tension within loop 24 using crimp-locking crimp 16 and releasable cable securing device 20 will be described below in more detail.

Referring to FIGS. 3 and 4, cable tensioner 18 has three main components: elongated shaft 26, first handle 28 and second handle 30. An important feature of tensioner 18 is that the main components of cable tensioner 18 may be formed from molded plastic. Thus, cable tensioner 18 is relatively inexpensive and may be discarded after only one use in a surgical procedure. This advantage of this aspect of the present invention is particularly important due to the increased concern with sterilization of surgical instruments to prevent the spread of AIDS and other diseases. Tensioner 18 may, of course, be formed from other materials such as aluminum.

First handle 28 is preferably secured to one end of elongated shaft 26. First handle (sometimes referred to as "fixed handle") 28 is generally configured to fit within the palm of a surgeon's hand (not shown). Elongated shaft 26 and first handle 28 cooperate to form a generally "T" shaped surgical tool.

Second handle 30 is slidably disposed on the exterior of elongated shaft 26 intermediate the ends thereof. Elongated shaft 26 has a generally rectangular cross section. First slot 32 is formed in the exterior of elongated shaft 26 intermediate the ends thereof. Second handle 30 includes opening 34 which is sized to fit over the portion of elongated shaft 26 containing first slot 32. Opening 34 cooperates with the exterior of elongated shaft 26 to allow second handle 30 to slide longitudinally over the exterior of elongated shaft 26.

The other end 36 of elongated shaft 26 has an opening 38 which provides a means for releasably securing a portion of a medical cable within end 36 of elongated shaft 26. A second slot 40 is provided in the exterior of elongated shaft 26 adjacent to and extending from end 36. As will be explained later in more detail, second slot 40 is provided to assist with attachment of a medical cable to second handle 30.

Second handle 30 and elongated shaft 26 also define a generally "T" shaped configuration. Second handle (sometimes referred to as "slidable handle") 30 preferably includes extensions 42 and 44 which are provided for engagement by the fingers of a surgeon's hand. Cable tensioner 18 is frequently used by first resting fixed handle 28 against the palm of a surgeon's hands and engaging extensions 42 and 44 with the fingers of the surgeon's hand. When the surgeon squeezes her fingers, second handle 30 will slide longitudinally towards first, fixed handle 28. This movement provides a direct tactile feedback with a 1:1 ratio between force applied to second handle 30 and tension applied to a medical cable 10 attached to tensioner 18.

Second handle 30 includes pawl 48 which is disposed within recess 50 of extension 42. Pin 52 is provided to secure pawl 48 within recess 50 and to allow pawl 48 to pivot with respect to pin 52 and the exterior of elongated shaft 26 adjacent thereto. First spring 54 is disposed within recess 50 and contacts a portion of pawl 48. Spring 54 cooperates with pivot pin 52 to bias pawl 48 to contact the exterior of elongated shaft 26 adjacent thereto. Therefore, pawl 48 will normally ride against the exterior of elongated shaft 26 and prevent movement of second handle 30 away from first handle 28.

Pawl 48 is preferably sized to fit within longitudinal slot 32 and to engage elongated shaft 26 therein. Spring 54 and pivot pin 52 cooperate with pawl 48 to allow longitudinal movement of second handle 30 towards first handle 28. In a similar manner spring 54, pivot pin 52 and pawl 48 cooperate with each other to prevent undesired movement of second handle 30 in the direction away from first handle 28.

Second handle 30 includes cleat 60 which is attached to the exterior of second handle 30 by pivot pin 62. Since second handle 30 is preferably formed from molded plastic, plate 64 is disposed between cleat 60 and the adjacent portions of second handle 30. Torsion spring 66 is provided to bias cleat 60 into contact with plate 64. As will be explained later in more detail, cleat 60 cooperates with plate 64 to trap a portion of medical cable 10 therebetween.

As shown in FIG. 1 cable tensioner 18 may be used with medical cable 10 to secure first loop 24 about selected portions of a patient's body such as vertebrae 12 and 14. Crimp-locking crimp 16 is preferably secured to a first end of medical cable 10 and loop 24 placed around the selected portion of the patient's body. Crimp-locking crimp 16 and the first end of medical cable 10 are then secured to end 36 of elongated shaft 26 opposite from first handle 28. A portion of medical cable 10 is placed within second longitudinal slot 40 in the exterior of elongated shaft 26 and slot 56 in second handle 30 adjacent to cleat 60. Second slot 40 in elongated shaft 26 and slot 56 in handle 30 cooperate with each other to align medical cable 10 with elongated shaft 26 and to allow engagement of a portion of medical cable 10 with cleat 60.

Cleat 60, torsion spring 66 and pivot pin 62 cooperate with each other to secure medical cable 10 to second handle 30. If desired, cleat 60 could be replaced by other mechanisms for trapping medical cable 10 with second handle 30. An example would be one or more set screws or locking nuts carried by second handle 30. Cleat 60 is preferred considering the ease of installing medical cable 10 therewith.

In FIG. 1 second medical loop 68 is shown installed on vertebrae 12 and 14 with crimp-locking crimp 16. For many procedures such as installing two medical cables 10 on selected vertebrae, it is preferable to alternately tighten and loosen the medical loops until the vertebrae are positioned as desired. A separate cable tensioner 18 may be used with each medical loop 24 and 68 to alternately increase and decrease the tension in the respective medical loops. But, releasable cable securing device 20 allows one tensioner 18 to be used to alternately adjust the tension in cable 10 as will be described in more detail below.

Pawl 48 normally prevents second handle 30 from sliding longitudinally away from first handle 28. By manually depressing pawl 48 into recess 50, pawl 48 is released from engagement with the adjacent portion of elongated shaft 26. When the surgeon depresses pawl 48, second handle 30 may slide longitudinally away from first handle 28 to release the tension in medical cable 10. This feature of the present invention allows the surgeon to provide the optimum tension in the loops on vertebrae 12 and 14. The ability of tensioner 18 to either increase or decease the tension in the medical loops allows obtaining the optimum forces on the portion of the patient's body which will be secured by the medical cables. This procedure is similar in many respects to tightening and loosening fasteners which are used to hold mechanical components together. After the desired amount of tension has been placed in loops 24 and 68, their respective crimp-locking crimps 16 may be compressed or crimped on the respective medical cables 10 to trap the tension. A portion of crimp-locking crimps 16 and their respective medical cables 10 may then be cut to allow removal of tensioner 18 and the remainder of medical cables 10. This crimping and cutting of crimps 16 may be accomplished with substantially one motion by using crimper-cutter 22 (FIG. 15).

A second embodiment 80 of cable tensioner 18 is shown in FIGS. 5 and 6. Cable tensioner 80 is preferably used with a medical cable 10 and a crimp-locking crimp 16 to trap the desired amount of tension in a loop formed by medical cable 10 and crimp 16. As explained for cable tensioner 20 (FIGS. 3–4), cable tensioner 80 may be used with medical cable 10 and crimp 16 to tighten first loop 24 around a selected portion of a patient's body and to trap the desired amount of tension within first loop 24.

Cable tensioner 80 has three main components: elongated shaft 82, first handle 84 and second handle 86. An important feature of this embodiment of the present invention is that the main components of cable tensioner 80 may be formed from aluminum or other suitable metals and composite materials which are appropriate for sterilization and repeated surgical use.

First handle 84 is preferably secured to one end of elongated shaft 82. First handle 84 is generally configured to fit within the palm of a surgeon's hand (not shown). Elongated shaft 82 and first handle 84 cooperate to form a generally "T" shaped surgical tool.

Second handle 86 is slidably disposed on the exterior of elongated shaft 82 intermediate the ends thereof. Elongated shaft 82 has a generally circular cross section. First slot 88 is formed in the exterior of elongated shaft 82 intermediate the ends thereof. A plurality of serrations 90 are provided within slot 88. Second handle 86 includes opening 92 which is sized to fit over the portion of elongated shaft 82 containing first slot 88. Opening 92 cooperates with the exterior of elongated shaft 82 to allow second handle 86 to slide longitudinally over the exterior of elongated shaft 82.

The other end 94 of elongated shaft 82 has an opening 96 which provides a portion of the means for releasably securing a portion of a medical crimp within end 94 of elongated shaft 82. A second slot 98 is provided in the exterior of elongated shaft 82 extending from end 94. As explained for second slot 40 of cable tensioner 20 of FIG. 3, slot 98 is provided to assist with attachment of a medical cable to second handle 86.

Second handle 86 and elongated shaft 82 also have a generally "T" shaped configuration. Second handle 86 preferably includes extensions 100 and 102 which are provided for engagement by the fingers of a surgeon's hand. Cable tensioner 80 is generally used by first resting fixed handle 84 against the palm of a surgeon's hands and engaging extensions 100 and 102 by the fingers of the surgeon's hand. When the surgeon squeezes his fingers, second handle 86 will slide longitudinally towards first, fixed handle 84.

The gripping aspect of tensioner 80 is analogous to that of tensioner 20. See FIG. 4. Second handle 86 includes pawl 48 disposed within recess 50 of extension 100. Pin 52 is provided to secure pawl 48 within recess 50 and to allow pawl 48 to pivot with respect to pin 52 and the exterior of elongated shaft 82 adjacent thereto. First spring 54 is disposed within recess 50 and contacts a portion of pawl 48. Spring 54 cooperates with pivot pin 52 to bias pawl 48 to contact the exterior of elongated shaft 82 adjacent thereto.

Pawl 48 is preferably sized to fit within longitudinal slot 88 and to engage serration 90 therein. Pawl 48 cooperates with first longitudinal slot 88 to prevent rotation of second handle 86 relative to shaft 82, and spring 54 and pivot pin 52 cooperate with pawl 48 to allow longitudinal movement of second handle 86 towards first handle 84. In a similar manner spring 54, pivot pin 52 and pawl 48 cooperate with each other and serration 90 to prevent undesired movement of second handle 86 in the direction away from first handle 84. As previously discussed for cable tensioner 20, pawl 48 allows controlled movement of second handle 86 to tighten and loosen tension in a medical cable 10 attached to cable tensioner 80.

Second handle 86 includes cleat 60 which is attached to the exterior of second handle 86 by pivot pin 62. Since second handle 86 is preferably formed from metal, plate 64 used with tensioner 20 is not required. Torsion spring 66 is provided to bias cleat 60 into contact with shoulder 104 formed on second handle 86. Cleat 60 cooperates with shoulder 104 on second handle 86 to trap a portion of medical cable 10 therebetween. See FIG. 7.

Cable tensioner 80 may be used with medical cable 10 to secure first loop 24 about selected portions of a patient's body such as vertebrae 12 and 14. Crimp-locking crimp 16 is preferably secured to one end of medical cable 10 and then loop 24 placed around the selected portion of the patient's body. Cable 10 is passed through a portion (bore 120) of crimp 16 and through releasable cable securing device 20. Releasable cable securing device 20 and an end of medical cable 10 are then secured to end 94 (36) of elongated shaft 82 (26) opposite from first handle 84 (28). A portion of medical cable 10 is placed within second longitudinal slot 98 (40) in the exterior of elongated shaft 82 (26). Second slot 98 (40) in elongated shaft 82 (26) aligns medical cable 10 with elongated shaft 82 and assists with engagement of a portion of medical cable 10 with cleat 60.

One of the differences between cable tensioner 80 and cable tensioner 18 of FIG. 3 includes gauge 108, which indicates the amount of force applied to second handle 86 after a medical cable has been secured to cable tensioner 80. The force measured by gauge 108 is an approximation of the tension applied to medical cable 10.

Elongated shaft 82 comprises first portion 82a attached to first handle 84 and second portion 82b, which is slidably disposed within first portion 82a. As shown in FIG. 6, second portion 82b of elongated shaft 82 preferably includes longitudinal passageway 110 extending partially therethrough. Alignment rod 112 is preferably attached to first portion 82a and extends from first handle 84 into longitudinal passageway 110. Biasing means or spring 114 is preferably disposed on the exterior of alignment rod 112 between first portion 82a and second portion 82b.

When one portion of a medical cable 10 is attached to end 94 of elongated shaft 82 and another portion of medical cable 10 is attached to second handle 86, movement of second handle 86 towards first handle 84 will result in longitudinal movement of second portion 82b relative to first portion 82a and compression of spring 114. Movement of second handle 86 towards first handle 84 will thus result in movement of gauge 108 relative to scale 116. The amount of force required to move second handle 86 towards first handle 84 is proportional to the spring constant of biasing means 114. Therefore, the position of gauge 108 on scale 116 is an indication of the force being applied to second handle 86 and to medical cable 10 attached to tensioner 80. Thus, cable tensioner 80 with gauge 108 provides an indication of the amount of tension being applied to a medical loop around a selected portion of the patient's body.

Scale 116 may be used to indicate increments of force such as 20, 40, 60 and 80 pounds. Pawl 48 cooperates with second handle 86 to trap the desired amount of tension within the attached medical cable as indicated by gauge 108.

An important feature of cable tensioner 80 is that spring 114 is located between second handle 86 and first handle 84 contained within second portion 82b of elongated shaft 82. This position for spring 114 minimizes potential adverse consequences from a failure of spring 114 and associated components.

Cable tensioners 20 and 80 may be used with various types of medical cable crimps, clamps and locks. Cable tensioners 20 and 80 are not limited to use with crimp 16 and releasable cable securing device 20. When used with releasable cable securing device 20, pawls 48 may not be required for use with second handles 30 and 86 to hold the desired amount of tension in the medical cable loop.

CRIMP-LOCKING CRIMP

Referring now to FIGS. 8 and 9, there is shown crimp-locking crimp 16 that is formed by crimp body 118 and crimp head 124. First longitudinal bore or channel 120 extends through crimp body 118 and head 124. Crimp 16 has neck 122 that may be formed as one integral part of crimp body 118 or attached to crimp body 118. Also formed as an integral part of crimp body 118, or attached to crimp body 118, is crimp head 124.

Crimp head 124 has a second bore or channel 126 extending through a portion of head 124 and offset from first longitudinal bore 120. Crimp 16 is preferably formed of titanium, but may also be formed of MP35N of Specification 562 of the American Society of Testing Materials, stainless steel, or ultra high molecular weight polyethylene.

Neck 122 may have several sections with varying outside diameters, e.g., 128, 130, and 132. Additionally, neck 122 may have a shoulder 134 to facilitate the attachment of surgical instruments to crimp body 118 to hold crimp 16 during surgery. In a preferred embodiment, crimp-locking crimp 16 may have neck 122 that is formed only by what is shown as first diameter section 128 in FIG. 8. When surgical cable 10 is passed through first longitudinal bore 120 and the desired tension has been applied to cable 10, neck 122 of crimp body 118 may be crimped, or plastically deformed, about cable 10 by applying a crimping force that may be generated by surgical pliers or a similar crimping tool so as to cause crimp 16 to hold and secure cable 10 by frictional forces developed between crimped neck 122 and the adjacent portion of cable 10. Neck 122 may be crimped or deformed on neck section 128. After crimping crimp 16, neck 122 also provides a convenient place to cut cable 10 and crimp 16. Neck 122 will then help prevent fraying of cable 10. Alternatively, crimper-cutter 22 (FIG. 15) may be used to crimp and cut neck 122 with substantially one motion and with only one instrument.

Referring now to FIG. 9, there is shown an elevational view of crimp-locking crimp 16. Crimp 16 has first longitudinal bore 120 that extends through crimp body 118 and head 124. Second bore 126 extends through a portion of head 124, and may have a first diameter 136 and a second diameter 138. First diameter 136 may have a diameter larger than the diameter of an enlarged cable termination such as ball termination on an end of cable 10. Second diameter 138 may be sized to have a diameter smaller than the diameter of termination of cable 10. First and second diameters 136 and 138 are thus sized to allow a cable termination, e.g., a ball termination, to pass into first diameter section 136 of second bore 126, but not through second diameter section 138 of second bore 126. First longitudinal bore 120 may also be sized to have sections of varying inside diameters, but with a minimum inside diameter larger than the outside diameter of cable 10. For example, first longitudinal bore 120 may have a first inside diameter section 142 (shown in hidden lines), second inside diameter section 144, and third inside diameter section 146.

RELEASABLE MEDICAL CABLE SECURING DEVICE

Referring to FIGS. 10 through 12, there is shown one embodiment of a cable securing apparatus or device 20. Cable securing device 20 has a body 202 formed to have a wedging chamber 204. Residing within wedging chamber 204 is wedging member 206. Wedging member 206 and chamber 204 form one example of wedging means used as part of device 20. Wedging member 206 may be a partial cylindrical member. Wedging member 206 is secured in chamber 204 by pin 208. Wedging member 206 may have a biasing chamber 210 containing biasing means or spring 212. Spring 212 interacts with wedging member 206 and a wall such as wall 214 of wedging chamber 204 to cause wedging member 206 to be biased against wall 214. Pin 208 is positioned on wedging member 206 such that wedging member 206 has an offset or off-centered pivot, i.e., a cam. As wedging member 206 is rotated clockwise with respect to the orientation shown in FIG. 10, wedging member 206 is unable to completely rotate about pin 208, but rather wedges against wall 214 of chamber 204.

Cable securing device 20 has a tensioner-gripping opening 216 about a first end 218 of cable secure 20. Tensioner gripping opening 216 is sized to mate with end 94 or 36 of tensioner 20 or 80. Tensioner gripping opening 216 is in communication with cable-receiving channel 220 which has an opening on a second end 222 of securing device 20. Cable-receiving channel 220 is in communication with and passes through wedging chamber 204.

In operation an end of cable 10 is threaded through cable securing device 20 by threading the cable end through channel 220 at end 222 and continuing through a portion of wedging chamber 204 and then through tensioner-gripping opening 216 at end 218. See FIG. 11. Once threaded through cable securing device 20, device 20 may function in one of two ways depending on the direction of force applied to cable 10. Additional operation occurs when wedging member 206 is forced away from wall 214 by the operator depressing portion 213 of wedging member 206.

Referring to FIG. 12, cable securing apparatus 20 is shown with a force applied to cable 10 in the direction indicated by arrow 226. The force applied in this direction urges wedging member 206 to rotate about pin 208 in a counter-clockwise direction. As cable 10 urges wedging member 206 in this direction, the gripping force supplied by wedging member 206 against wall 214 is reduced, and cable 10 is allowed to move in the same direction as the force, i.e., the direction of arrow 226. The wedging force is reduced because biasing spring 212 forces wedging member 206 towards wall 214, which normally sandwiches cable 10 therebetween, and as cable 10 is urged in the direction of arrow 226, the frictional forces between cable 10 and wedging member 206 cause member 206 to be urged counter-clockwise. As wedging member 206 is urged counter-clockwise, the force that applies to cable 10 is reduced because the outer perimeter of wedging member 206 is pulled away from the point of tangential contact with cable 10 proximate wall 214; this latter effect is due to the off-centered orientation of pin 208.

Referring to FIG. 11, there is shown cable securing device 20 with a force applied to cable 10 in the direction indicated by arrow 224. With a force applied in this direction, the cable is urged in the direction of arrow 224 which because of frictional forces between wedging member 206 and cable 10 caused by biasing spring 212, wedging member 206 is urged in a clockwise direction. As wedging member 206 moves in a clockwise direction, the linear distance between pin 208 and the point of tangential contact between cable 10 and wedge member 206 increases, and thus, cable 10 becomes wedged against wall 214 by member 206.

As demonstrated by FIGS. 11 and 12, cable securing device 20 allows a tension to be applied in the direction of arrow 226 with little or no resistance from a device 20, but when the tensioning force is removed so that the resultant force is in the direction shown by arrow 224 in FIG. 11, securing device 20 will maintain the tension that was applied. When it is desirable to remove securing device 20, wedging member 206 may be manually pulled away from wall 214 by overcoming the forces generated by biasing spring 212 by depressing portion 213; this will reduce the frictional forces on cable 10 between wedging member 206 wall 214 to allow the cable to be removed. Cable securing device 20 may be used as part of a system for securing loops 24 and 68 about a desired portion of a patient's body as shown in FIG. 1.

Referring now to FIGS. 13 and 14, an alternative embodiment of cable securing device 20 is shown. Cable securing device 20 of FIGS. 13 and 14 has body 202. Formed in body 202 is cable-receiving channel 220 which is in communication with wedging chamber 204 and opening 228. Opposite second end 222 is first end 218. Body 202 has a shaft-receiving chamber 230 with shaft 232 residing therein and movable with respect to chamber 230.

A first portion of wedging chamber 204 is formed to have tapered wall 234. A first end of shaft 232 has a wedging member 206 secured thereto. Wedging member 206 for this second embodiment may be similar to a frusto-conical shaped member. Wedging member 206 has a back surface 233. A portion of body 202 that forms shaft-receiving chamber 230 also forms wall 236. A biasing spring 212 is provided along shaft 232 between back surface 233 and wall 236 that urges wedging member 206 towards first end 222.

Cable securing device 20 of FIGS. 13 and 14 has a biasing release member 238. Biasing release member 238 pulls wedging member 206 away from first end 222 and away from tapered wall 234. Bias release member 238 may be, for example, an oval-shaped member that when in the position shown in FIG. 14 is provided in an oval opening in body 202 from which it may be pulled away from first end 222 out of body 202 and twisted such that when released, the biasing release member 238 will not return into the opening. This allows securing device 20 to remain in a condition where it does not wedge when so desired. This position is desirable when threading cable 10 through channel 220, chamber 204 and out at opening 228 or for removing the cable.

Like securing device 20 of FIGS. 10 through 12, securing device 20 of FIGS. 13 through 14 allow cable 10 to move in one direction but not in another according to the direction of the net force applied. Referring to FIG. 14, it can be seen that as cable 10 is urged in the direction shown by arrow 240, lip 242 of wedging member 206 and surface 244 of wedging member 206 grip cable 10 and urge it farther into tapered wall 234 thus providing additional frictional forces between tapered wall 234 and conical-shaped wedging member 206 that secure cable 10 and do not allow it to move in the direction of arrow 240. Conversely, when cable 10 is urged in the direction shown by arrow 246, cable 10 is allowed to move when the force applied is greater than a predetermined force that is a function of the force supplied by biasing spring 212; the frictional forces between cable 10 and wedging member 206 urge wedging member 206 towards second end 218. Once the force with which wedging member 206 is urged towards second end 218 overcomes the force provided by biasing spring 212, wedging member 206 will move towards end 218 and any wedging force supplied between wedging member 206 and wall 234 is released and cable 10 is allowed to move freely in the direction of arrow 246.

CRIMPER-CUTTER

Referring to FIG. 15, there is shown crimper-cutter 22. Crimper-cutter 22 is used to crimp a crimp-locking crimp 16 while also cutting a portion of crimp 16 with the same instrument. Crimper-cutter 22 has two main components: crimping-cutting head 250 and block-head 252. Crimping-cutting head 250 is formed of a body 254 which has two portions 256 and 257 that form a crimping channel 258. Crimping-cutting head 250 also has a blade member 260 with an edge 262.

From the frame of reference of cutting-cutting head 250, block-head 252 moves towards crimping channel 258 in the direction shown by arrow 265, which represents a force applied to block-head 252. Block-head 252 is moved relative to crimping-cutting head 250 as indicated by means known in the art, e.g., plier-like handles 264. As handles 264 are moved together by the hand of the surgeon, block-head 252 is moved toward crimping-cutting head 250.

To use crimper-cutter 22, neck 122 of crimp 16 is placed at the opening of crimping channel 258, which is sized smaller than neck 122 by a predetermined amount. Neck 122 of crimp 16 is positioned so that a portion of neck 122 extends out of crimping channel 258 and overhangs edge 262 of blade member 260. Handles 264 are then urged towards each other by the user which because rotation about pin 266 urges block-head 252 toward crimping-cutting head 250. Block-head 252 contacts neck 122 of crimp 16 and forces it into crimping channel 258 which plastically deforms neck 122 thereby crimping cable 10 within crimp 16. As block-head 252 continues to move into crimping channel 258, a portion of neck 122 on crimp 16 contacts edge 262 of blade member 260, and as block-head 252 continues to move, cable 10 and neck 122 are cut by edge 262. Thus, with the one action of moving handles 264 together, neck 122 of crimp 16 is crimped and cable 10 and crimp 16 are cut.

ADDITIONAL DETAILS OF THE SYSTEM AND METHOD

One application of the system of the present invention is to apply a loop about a desired portion of a patient's body such as vertebrae 12 and 14. To secure loop 24 about vertebrae 12 and 14, the surgeon would first thread a first end of cable 10 through opening 126 in crimp 16 (See FIG. 8), then pass the cable sub-lamina of vertebrae 12 and 14, then pass the same cable end through bore 120 of crimp 16. The second end of cable 10 has a cable termination that is secured in opening 126. After being passed through longitudinal bore 120 of crimp 16, first end of cable 10 is threaded through cable-receiving channel 220 of cable securing device 20 with the first end of cable 10 exiting at 216 (FIG. 10). The first end of cable 10 is then threaded through opening 38 of cable tensioner 18 as previously described and end 36 of tensioner 18 is secured in opening 216 of cable securing device 20.

The surgeon then uses tensioner 18 to apply the desired tension to loop 24. During this process, cable securing device 20 allows the tension that the surgeon applies to be maintained even if the surgeon removes tensioner 18 to allow the surgeon to then tighten or loosen another loop such as loop 68. Once the desired tension is placed in loop 24, crimp 16 may be crimped and cut. This latter task may be accomplished with crimper-cutter 22. To crimp and cut with this instrument, neck 122 of crimp 16 is placed over crimping channel 258 and then block-head 252 forces neck 122 into channel 258 thereby crimping neck 122. As head 252 is continued to be urged into crimping channel 258, neck 122 is cut by edge 262 of blade member 260. Once cable 10 and neck 122 are cut, tensioner 18, remaining portion of cable 10, and cable securing device 20 may be removed. The end result is a loop 24 formed by cable 10 and secured with crimp 16 and having a desired tension in loop 24.

Although the present invention in its advantages have been described in detail, it should be understood that various changes, substitutions, and alterations can be made therein without departing from the spirit and scope of the invention.

What is claimed is:

1. A system including a medical cable for allowing an operator to secure the medical cable in a loop about a specified portion of a patient's body with a desired tension, the system comprising:

a tensioner for applying the desired tension to the cable after looping the cable around the desired portion of the patient's body;

a crimp-locking crimp attached to a first end of the cable and formed to have a cable-receiving bore for receiving the cable after the loop is formed;

a neck provided on the crimp-locking crimp for use in securing the cable;

a releasable cable securing device for allowing movement of the cable in only one direction; and a crimper-cutter for crimping and cutting the neck of the crimp-locking crimp to secure the loop in the cable.

2. The system of claim 1 wherein the crimper-cutter comprises:

a crimper-cutting head formed with a crimping channel for receiving the neck of the crimp-locking crimp;

a block head formed to mate with the crimping channel;

means for engaging the crimper-cutting head and the block head; and a cutting edge coupled to the crimper-cutting head for cutting a portion of the neck of the crimp-locking crimp as the block head reaches a bottom portion of the crimping channel.

3. A system including a medical cable for allowing an operator to secure the medical cable in a loop about a specified portion of a patient's body with a desired tension, the system comprising:

a tensioner for applying the desired tension to the cable after looping the cable around the desired portion of the patient's body, said tensioner comprising:

an elongated shaft having a first handle secured to one end of the shaft, a second handle slidably disposed on the shaft intermediate the ends thereof, means for releasably securing a portion of the medical cable adjacent to the other end of the shaft opposite from the first handle, and means for securing another portion of the medical cable to the second handle;

a crimp-locking crimp attached to a first end of the cable and formed to have a cable-receiving bore for receiving the cable after the loop is formed;

a neck provided on the crimp-locking crimp for use in securing the cable; and a releasable cable securing device for allowing movement of the cable in only one direction.

4. The system of claim 3 wherein the releasable cable securing device comprises:

a body having a cable-receiving channel extending through the body; and a wedging means for locking the cable when a first net force is applied to the cable in one direction relative to the cable-receiving channel and allowing the cable to move when a second net force is applied to the cable in a second direction relative to the cable-receiving channel.

5. The system of claim 4 wherein the wedging means of the releasable cable securing device comprises:

a wedging member; and a wedging chamber formed in the body of the securing device, the wedging chamber intersecting with at least a portion of the cable receiving channel and having the wedging member disposed within the wedging chamber.

6. The system of claim 5, wherein the wedging member is a partial cylindrical member with an off center pivot point.

7. The system of claim 3, wherein the crimp-locking crimp comprises:

a crimp body having a first longitudinal bore extending through the crimp body and the first bore having a diameter larger than the outside diameter of the cable so that the cable can be inserted into the first longitudinal bore;

a head on one end of the crimp body with the first longitudinal bore extending through the head;

a neck for developing a securing force about the medical cable when crimped, the neck located on one end of the crimp body with the first longitudinal bore extending through the neck an enlarged cable termination or one end of the medical cable; and a second bore extending through the head and offset from the first longitudinal bore, the second bore having an inside diameter larger than the outside diameter of the cable and smaller than the diameter of the enlarged cable termination.

8. The system of claim 3, wherein the tensioner further comprises:

the elongated shaft having a generally rectangular cross section;

the second handle having an opening sized to allow the second handle to slide longitudinally over the exterior of the elongated shaft; and means for preventing longitudinal movement of the second handle in one direction.

9. The system of claim 3, wherein the crimp-locking crimp comprises:

a crimp body having a first longitudinal bore extending through the crimp body;

a head on one end of the crimp body with the first longitudinal bore extending therethrough; and a second bore extending through the head and offset from the first longitudinal bore.

10. The system of claim 9, wherein the crimp body and the head comprise MP35N alloy.

11. The system of claim 9, wherein the crimp body and the head comprise stainless steel.

12. An apparatus for crimping and cutting a crimp-locking crimp and a cable disposed therein, the apparatus comprising:

a first head formed to have a crimping channel therein;

a blade member attached to the first head proximate a first end of the first head;

a second head formed to mate with the crimping channel of the first head;

an engaging means for moving the first head toward the second head including a pair of handles with the first head attached to an end of one of the handles and the second head attached to an adjacent end of one of the other handles with a pin disposed intermediate the ends of the handles to allow rotation of the handles with respect to each other; and wherein the crimping channel is adapted to secure the crimp-locking crimp to the cable by plastically deforming the crimp-locking crimp around the cable when the first head and second head mate under the influence of the engaging means, and the blade member is adapted to cut the crimp-locking crimp and the cable when the crimp-locking crimp reaches a lower portion of the crimping channel.

* * * * *